(12) United States Patent
Loos

(10) Patent No.: US 6,238,333 B1
(45) Date of Patent: May 29, 2001

(54) REMOTE MAGNETIC MANIPULATION OF NERVOUS SYSTEMS

(76) Inventor: Hendricus G. Loos, 3019 Cresta Way, Laguna Beach, CA (US) 92651

( * ) Notice: Subject to any disclaimer, the term of this patent is extended or adjusted under 35 U.S.C. 154(b) by 0 days.

(21) Appl. No.: 09/371,289

(22) Filed: Aug. 10, 1999

Related U.S. Application Data

(63) Continuation-in-part of application No. 08/486,918, filed on Jun. 7, 1995, now Pat. No. 5,935,054.

(51) Int. Cl.[7] ....................................... A61N 2/00
(52) U.S. Cl. ............................................. 600/9
(58) Field of Search ............................... 600/9–15

(56) References Cited

U.S. PATENT DOCUMENTS

| | | | |
|---|---|---|---|
| 3,678,337 | 7/1972 | Grauvogel | 317/4 |
| 4,197,851 | 4/1980 | Fellus | 128/422 |
| 4,537,181 | * 8/1985 | Shalhoob et al. | 600/9 |
| 4,611,599 | 9/1986 | Bentall | 128/422 |
| 4,727,857 | * 3/1988 | Horl | 600/9 |
| 5,667,469 | * 9/1997 | Zhang et al. | 600/9 |
| 6,001,055 | * 12/1999 | Souder | 600/9 |

OTHER PUBLICATIONS

P. Lindemann, The Megabrain Report, vol. 1, #2, p. 34–35 (1990).
P. Limdemann, The Megabrain Report, vol. 1, #1, p. 30–31 (1990).

* cited by examiner

Primary Examiner—John P. Lacyk

(57) ABSTRACT

Apparatus and method for remote manipulation of nervous systems by the magnetic dipole field of a rotating bar magnet. Reliance on modulation of spontaneous spiking patterns of sensory nerve receptors, and exploitation of a resonance mechanism of certain neural circuits, allows the use of very weak magnetic fields. This, together with the large magnetic moments that can be obtained with a permanent bar magnet, makes it possible to effectively manipulate the nervous system of a subject over a distance of several hundred meters, using a small portable battery-powered device. The method can be used in law enforcement for standoff situations.

8 Claims, 3 Drawing Sheets

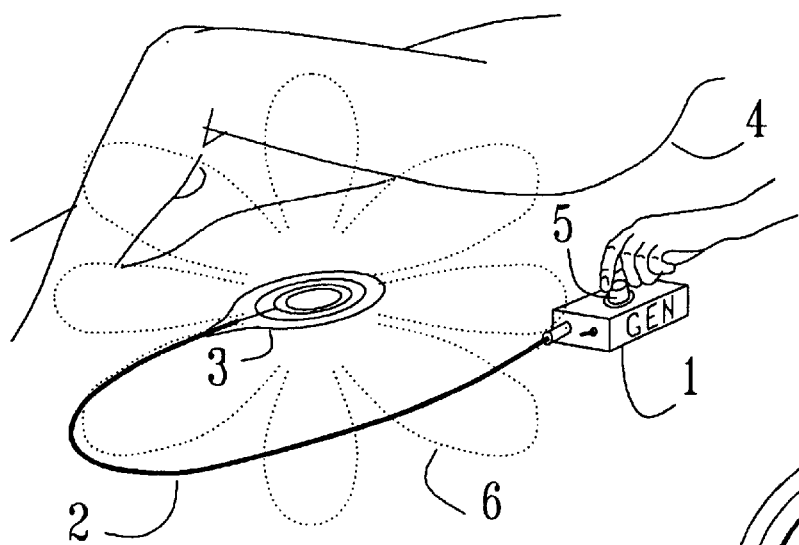
FIG. 6
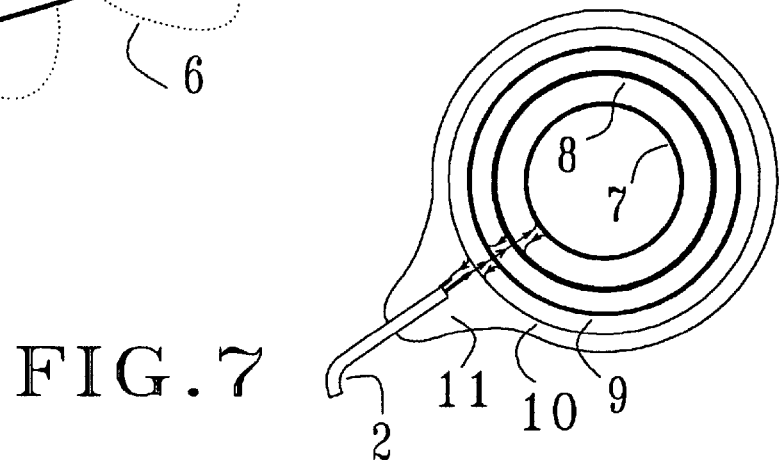
FIG. 7
FIG. 8
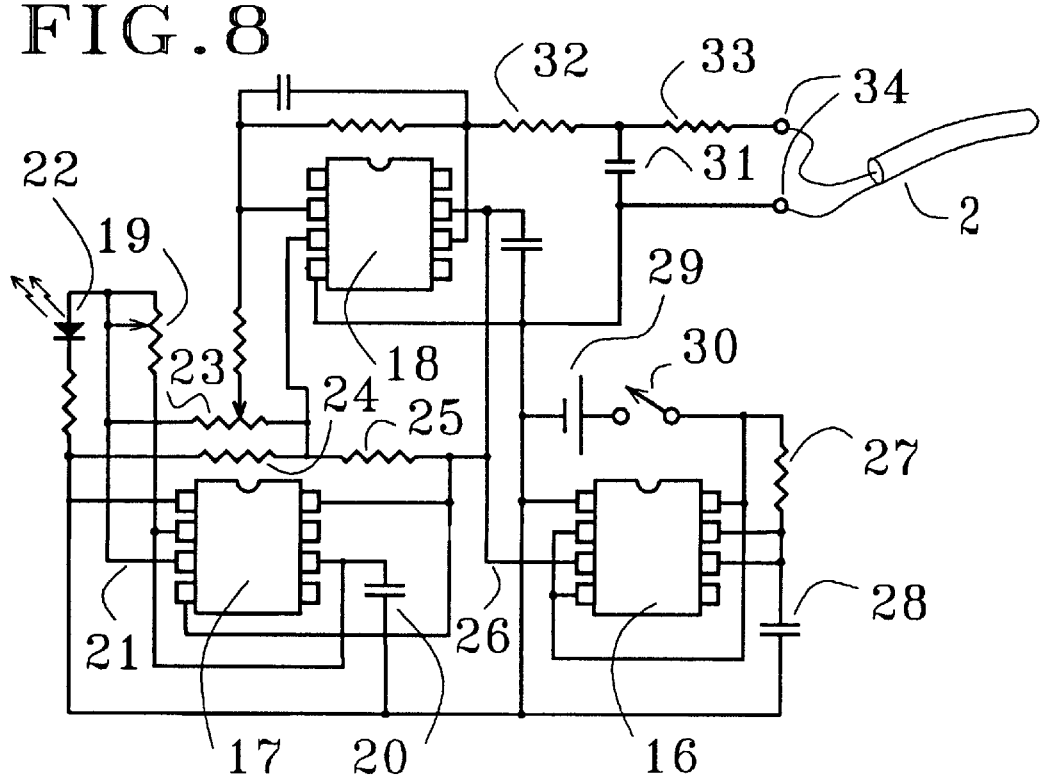

US 6,238,333 B1

REMOTE MAGNETIC MANIPULATION OF NERVOUS SYSTEMS

Continuation in Part of application Ser. No. 08/486,918, Jun. 7, 1995, U.S. Pat. No. 5,935,054.

BACKGROUND OF THE INVENTION

The invention relates to stimulation of nerves by pulsed magnetic fields. Such fields induce in the body of an exposed subject eddy currents that are proportional to their rate of change. The currents may cause classical nerve stimulation wherein the nerve membrane is depolarized enough for the nerve to fire. At low frequencies, such a mechanism requires rather large magnetic fields. Fortunately, low-frequency magnetic manipulation of the nervous system is possible by another mechanism which allows the use of very much weaker fields. Instead of relying on causing the firing of normally quiescent nerves, the method uses modulation of the spiking patterns of spontaneously firing nerves. That this can be done with very small tissue electic fields was discussed more than four decades ago by C. A. Terzuolo and T. H. Bullock in "Measurement of Imposed Voltage Gradient Adequate to Modulate Neuronal Firing", Proceedings of the National Academy of Sciences U.S.A., Physiology, 42, 687 (1956). The effect can be exploited in magnetic as well as in electric stimulation, because the physiological effects of the former are solely due to the electric field that is induced by the rate of change of the magnetic field, and by the electric polarization that occurs as the consequence of the induced eddy currents.

The human nervous system exhibits a sensitivity to certain low-frequency stimuli, as is evident from rocking a baby or relaxing in a rocking chair. In both cases, the maximum soothing effect is obtained for a periodic motion with a frequency near ½ Hz. The effect is here called "the ½ Hz sensory resonance". In the rocking response, the sensory resonance is excited principally by frequency-coded signals from the vestibular end organ. However, the rocking motion also induces body strains, and these are detected by stretch receptors residing in the skin and elsewhere in the body. In addition, relevant signals may originate from thermal receptors which report skin temperature fluctuations caused by air currents that are induced by the rocking motion. All these receptors employ frequency coding in their sensory function, and it must be that their signals are combined and compared in the brain with the vestibular nerve signals in an assessment of the somatic state. One may thus expect that the sensory resonance can be excited not only through the vestibular nerve, but also separately through the other sensory modalities mentioned. This notion is supported by the observation that gently stroking of a child with a frequency near ½ Hz has a soothing effect. Further support derives from the successful excitation of the ½ Hz sensory resonance by weak external electric fields, as discussed in "Method and Apparatus for Manipulating Nervous Systems", U.S. Pat. No. 5,782,874. The ½ Hz sensory resonance involves the autonomic nervous system, and it can be used to induce relaxation, sleepiness, or sexual excitement, depending on the precise stimulation frequency and the affected afferent nerves. Another sensory resonance has been found at about 2.4 Hz; it involves the cortex since it can slow the speed of silently counting from 100 to 60, with the eyes closed, as discussed in the '874 patent and in U.S. Pat. No. 5,800,481. For both electric field and thermal stimulation, prolonged exposure to fluctuating electric fields near 2.4 Hz has been found to have a sleep-inducing and dizzying effect. The same physiological effect is expected for pulsative magnetic stimulation, since electric fields are induced in the tissue by the changing magnetic field. When using the nerve modulation method, reliance on resonance mechanisms further reduces the stimulation strength required for manipulating the nervous system.

SUMMARY

Oscillatory magnetic fields induce electric fields in exposed biological tissue and can therefore act on nerves. Considerable tissue electric fields are needed to cause firing of otherwise quiescent nerves, but very much smaller fields suffice for modulation of spontaneous nerve spiking. Still weaker fields can be used for exciting resonances in certain neural circuits through evoked signals from afferent somatosensory nerves which carry the modulated spiking patterns to the brain.

It has been found that, in this manner, weak oscillatory magnetic fields with an amplitude between 5 femtotesla and 50 nanotesla can be used for manipulating the human nervous system, when the fields are tuned to certain frequencies near ½ Hz that cause excitation of sensory resonances. Observable physiological consequences of the resonance include ptosis of the eyelids, relaxation, sleepiness, and sexual excitement, depending on the precise frequency used, and on the location and duration of the magnetic field application.

Both topical and systemic field administration have been found effective. For the latter case the field can be produced over a considerable distance by a rotating permanent magnet that has a large magnetic moment. This makes it possible to manipulate a subject's nervous system over a range of several hundred meters, such as to cause relaxation and drowsiness. The method can be used in law enforcement for standoff situations.

Simple devices which use a rotating bar magnet are disclosed. Multiple rotating bar magnets can be used, and the phase angles of the magnets may then be arranged to cause constructive interference of the magnetic fields induced in the subject.

DESCRIPTION OF THE DRAWINGS

FIG. 6 illustrates an embodiment for topical application of an oscillating magnetic field for the excitation of a sensory resonance.

FIG. 7 shows a multipole coil for the generation of a localized magnetic field for topical field administration.

FIG. 8 shows a near-sine wave generator with automatic shutoff, suitable for driving magnetic coils.

DETAILED DESCRIPTION

It has been found in our laboratory that a weak oscillatory magnetic field can be used to excite the ½ Hz sensory resonance. Sinusoidal magnetic fields have been observed to induce ptosis of the eyelids, relaxation, sleepiness, a "knot" in the stomach, a soft warm feeling in the stomach, a tonic smile, sudden loose stool, and sexual excitement, depending on the precise frequency used, the part of the body exposed, and the strength and duration of the field application. The frequencies for these effects are all close to ½ Hz. The physiological effects are experienced after the subject has been exposed to the field for an extended time, ranging from minutes to hours. Even for optimum frequency, the effects have been observed only for weak fields with amplitudes roughly in the range from 5 femtotesla to 50 nanotesla.

Use of square waves for the time dependence of the magnetic field gives similar results, but there is a peculiar harsh feeling that is absent for sine waves, attributed to the strong higher harmonics in the square wave.

The effects have been obtained with systemic field applications as well as with topical applications of a localized magnetic field, either administered to the head or to body regions away from the head; successful excitation in the latter case shows that the magnetic field can act on somatosensory nerves.

Fixing all experiment parameters but the magnetic field amplitude, the described physiological effects are observed only for field amplitudes in an interval, called "the effective intensity window". This feature of sensory resonances may be understood as due to nuisance-guarding neural circuitry which blocks impertinent repetitive sensory signals from higher processing. For the guarding circuitry to spring in action, the amplitude of the nuisance signals needs to exceed a certain threshold. This explains the upper boundary of the effective intensity window. The lower boundary of the window is simply due to the detection threshold for the sensory signals.

Figure 3:
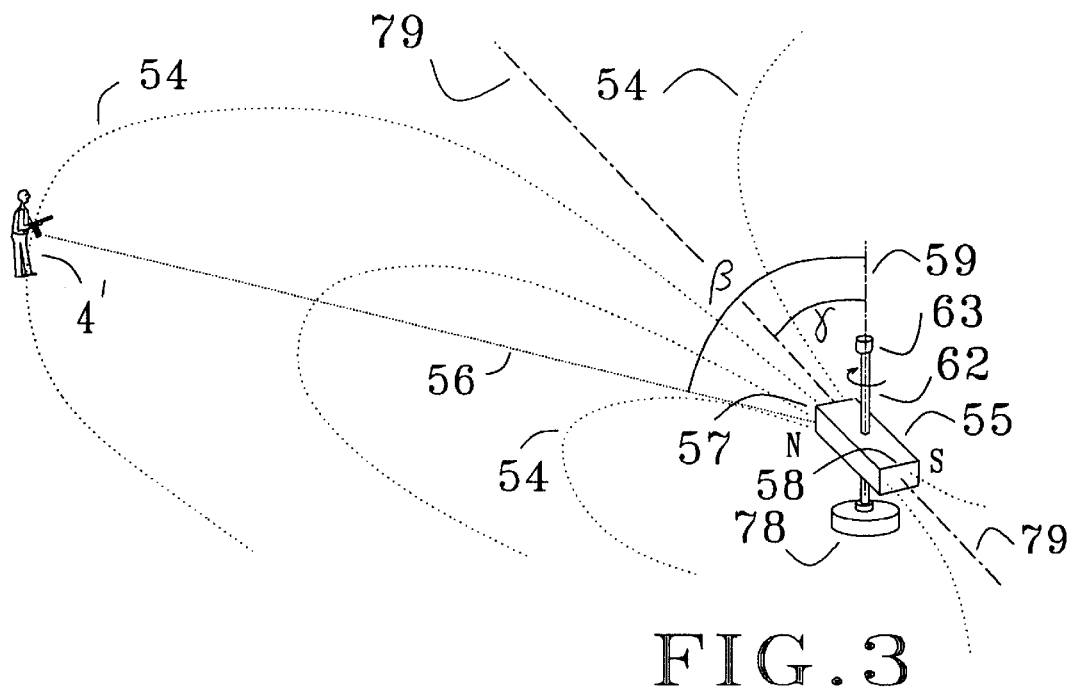
FIG. 3 illustrates the rotating magnet method of projecting a time-varying dipole field upon a remote subject.
Figure 4:
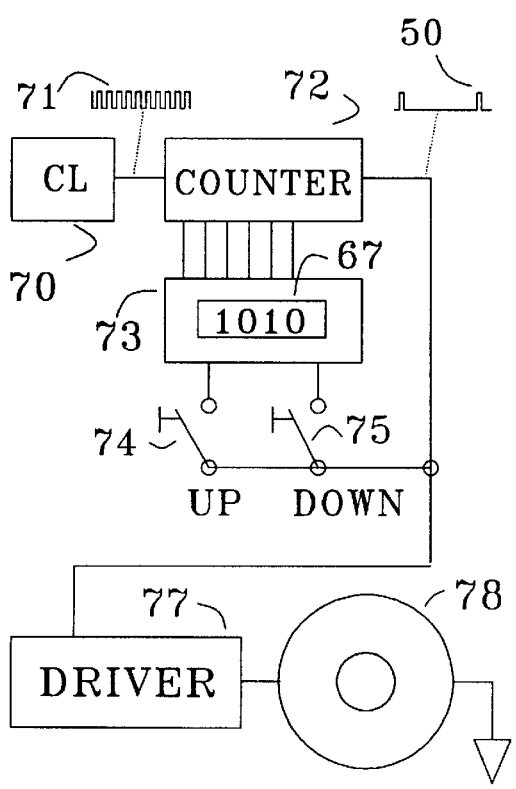
FIG. 4 shows a drive circuit for the rotating magnet of FIG. 3.
Figure 5:
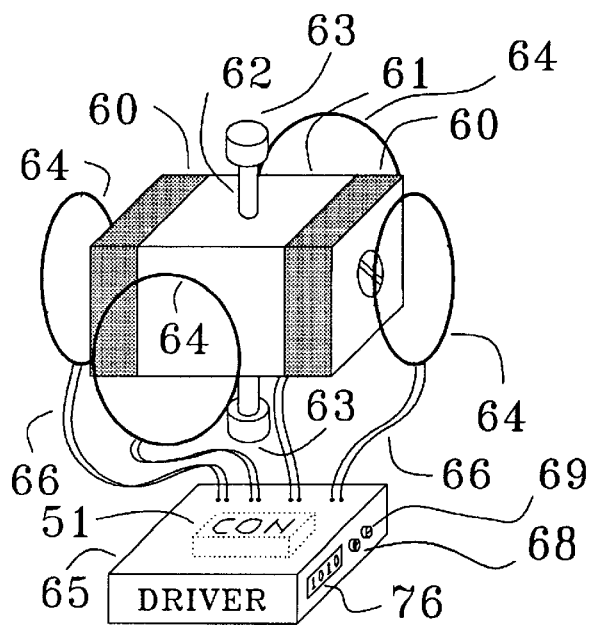
FIG. 5 shows the preferred embodiment wherein the bar magnet rotation is caused by coils that induce magnetic fields which act directly on the bar magnet.

Systemic application of an approximately uniform rotating magnetic field at a frequency of 0.55 Hz and an amplitude of 2.3 nanotesla results in wooziness after about two hours of exposure; sexual excitement sets in about one hour later. The rotating magnetic field for this experiment was obtained by using a 33 rpm phonograph turntable which carries two permanent magnets with a total magnetic moment of 6.5 $Am^2$; the distance to the subject was 10.4 m. Allthough the use of the 33 rpm turntable is convenient, the frequency is not quite optimum for excitation of the ½ Hz sensory resonance. This explains the long exposure times needed to obtain a physiological response, accounting for the drift in resonance frequencies described in the '874 patent. Other experiments with systemic application of magnetic fields, albeit with slightly greater nonuniformity, have given results that are similar to those obtained with topical applications of sharply localized fields. The rotating magnet device shown in FIGS. 3–5 is discussed later in the context of law enforcement in standoff situations, but it may be employed for therapeutic purposes as well. The device can be used for collective treatment of a number of subjects in a single building or in a complex of buildings.

The physiological effects induced by the magnetic field over an extended time often linger for as much as an hour after ending the application. This suggests that the endocrine system is affected, either directly or indirectly.

Experiments with magnetic field therapy for mild insomnia have been conducted for over 200 nights, using a variety of voltage generators and coils. Among the various wave forms, sine waves have given the best results when used with very weak fields, of the order of 10 femtotesla, applied to the lower lumbar region of the body. A typical frequency used in these experiments is 0.49 Hz. A virtue of the very weak fields is that habituation to the stimulus is at a minimum, so that the treatment remains effective over many nights. Habituation is further minimized by using multipole magnetic fields. Such fields are sharply localized, and they have strongly nonuniform spatial distributions. As a result, the evoked somatic signals received by the brain from the various parts of the body are strongly nonuniform and localized. Therefore, changes in sleep position cause a large variety of sensory patterns of limited duration. Another successful approach for controlling habituation is to limit the magnetic field application to half an hour or so; larger field strengths can then be used.

Experiments for inducing sexual excitement by sinusoidal magnetic fields have been performed using topical as well as systemic field application. Topical application of a sinusoidal multipole magnetic field of order six to the lower lumbar region, with maximum field amplitude of about one nanotesla, usually causes after about 13 minutes of exposure an erection that can be maintained as long as an hour. Effective frequencies depend somewhat on physiological conditions, but a typical frequency for obtaining this effect is 0.62 Hz.

The experiments suggest a method and apparatus for manipulating nervous systems by fluctuating magnetic fields. The method has two fundamental features: use of modulation of spontaneous spiking activity of certain types of somatosensory receptors, and the exploitation of sensory resonances. Both these features allow reduction of the magnetic field amplitude, and in combination they make possible small and compact battery-powered devices that can be used by the public for induction of relaxation, sleepiness, or arousal, and clinically for the control and perhaps the treatment of tremors and seizures, and disorders of the autonomic nervous system, such as panic attacks.

A sensory resonance has been found near 2.4 Hz, that can be excited by weak pulsed external electric fields, or by weak heat pulses delivered to the skin, or by subliminal acoustic pulses, as discussed respectively in U.S. Pat. Nos. 5,782,874 and 5,800,481, and U.S. patent application Ser. No. 08/961,907. It is expected that this resonance can also be excited magnetically. Other sensory resonances may perhaps be found, with frequencies below 45 Hz.

An embodiment of the invention is shown in FIG. 6, where a voltage generator 1, labeled "GEN", is connected through a thin coaxial cable 2 to a coil assembly 3; the latter is placed some distance beneath the subject 4 near the body region selected for topical field application. The frequency of the voltage generator 1 can be manually adjusted with the tuning control 5, so that by manual scanning frequencies can be found at which sensory resonances are excited. Upon being energized by the generator 1, the coil assembly 3 induces a magnetic field with field lines 6, which at large distances is a multipole field. The coil 3 can be conveniently placed under the mattress of a bed. The setup of FIG. 6 has been employed in the insomnia therapy experiments and the sexual arousal experiments discussed.

A simple near-sine-wave generator suitable for driving the coil of FIG. 6 is shown in FIG. 8. The battery-powered generator is built around two RC timers 16 and 17, and an operational amplifier 18. Timer 17 (Intersil ICM7555) is hooked up for astable operation; it produces a square wave voltage with a frequency determined by potentiometer 19 and capacitor 20. The square wave voltage at output 21 drives the LED 22, and serves as the inverting input for the amplifier 18 (MAX480), after voltage division by potentiometer 23. The noninverting input of amplifier 18 is connected to an intermediate voltage produced by resistors 24 and 25. Automatic shutoff of the voltage at point 26, that powers the timer and the amplifier, is provided by a second timer 16 (Intersil ICM7555), hooked up for monostable operation. The shutoff occurs after a time interval determined by resistor 27 and capacitor 28. Timer 16 is powered by a three-volt battery 29, controlled by a switch 30. The amplifier 18 is hooked up as an integrator; additional integration is performed by the capacitor 31 and resistor 32. The resistor 33 limits the output current to the terminals 34 that are connected to the coil assembly by the coaxial cable 2.

For topical magnetic field applications, such as illustrated by FIG. 6, it is important to have a sharply localized magnetic field, either to avoid unwanted exposure of body regions away from the region of application, or to decrease habituation, as discussed above. A planar coil assembly suitable for the induction of such sharply localized magnetic field is shown in FIG. 7. The assembly consists of four coils, referred to as 7, 8, 9, and 10, with alternating winding directions. The series assembly of coils is connected to the coaxial feed cable 2. The coils 7–10 are mounted on an adhesive sheet 11 of insulating material, and the assembly is covered with adhesive tape. The coil diameters are proportional to 1, √2, √3, and 2, and the number of windings are respectively proportional to 4, −6, 4, and 1, where positive and negative numbers denote respectively clockwise and counterclockwise windings. For clarity the connecting wires between coils are shown as running at some distance from each other, but these wires should actually be laid very close together, in order that their induced magnetic fields cancel each other as much as possible. With this understanding, the coil assembly of FIG. 7 can be shown to induce at large distances a magnetic field that falls off as the ninth power of distance.

Eddy currents are induced in tissue by time-varying magnetic fields. Time dependence can of course be achieved by rotating an otherwise steady magnetic field. Since large steady fields can be obtained from a permanent magnet without spending energy, it is sensible to produce the rotating field by mechanically rotating a permanent magnet. There are several patents, such as U.S. Pat. Nos. 4,727,857 and 5,667,469, wherein such an approach is used for topically inducing therapeutic low-frequency eddy currents by means of equipment placed closely adjacent to the patient's skin.

Figure 1:
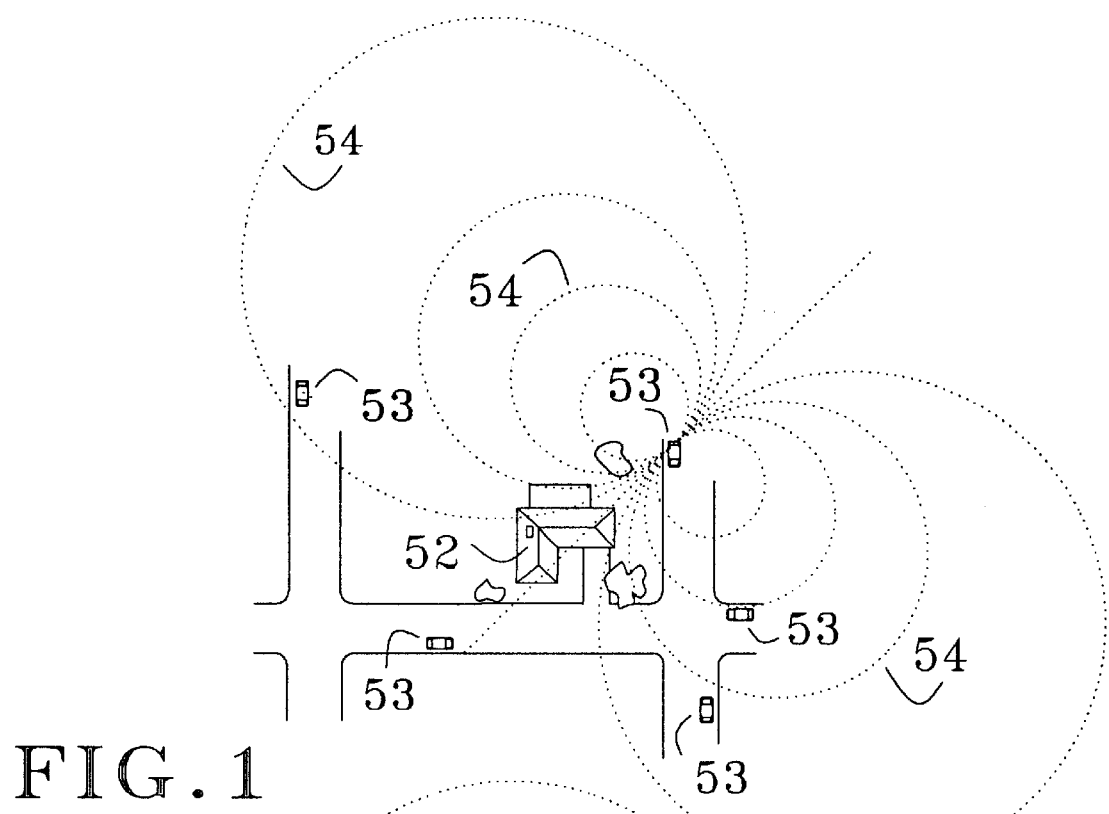
FIG. 1 illustrates an embodiment as a non-lethal weapon to be used in law enforcement, showing the dipole magnetic field projected upon a standoff site.
Figure 2:
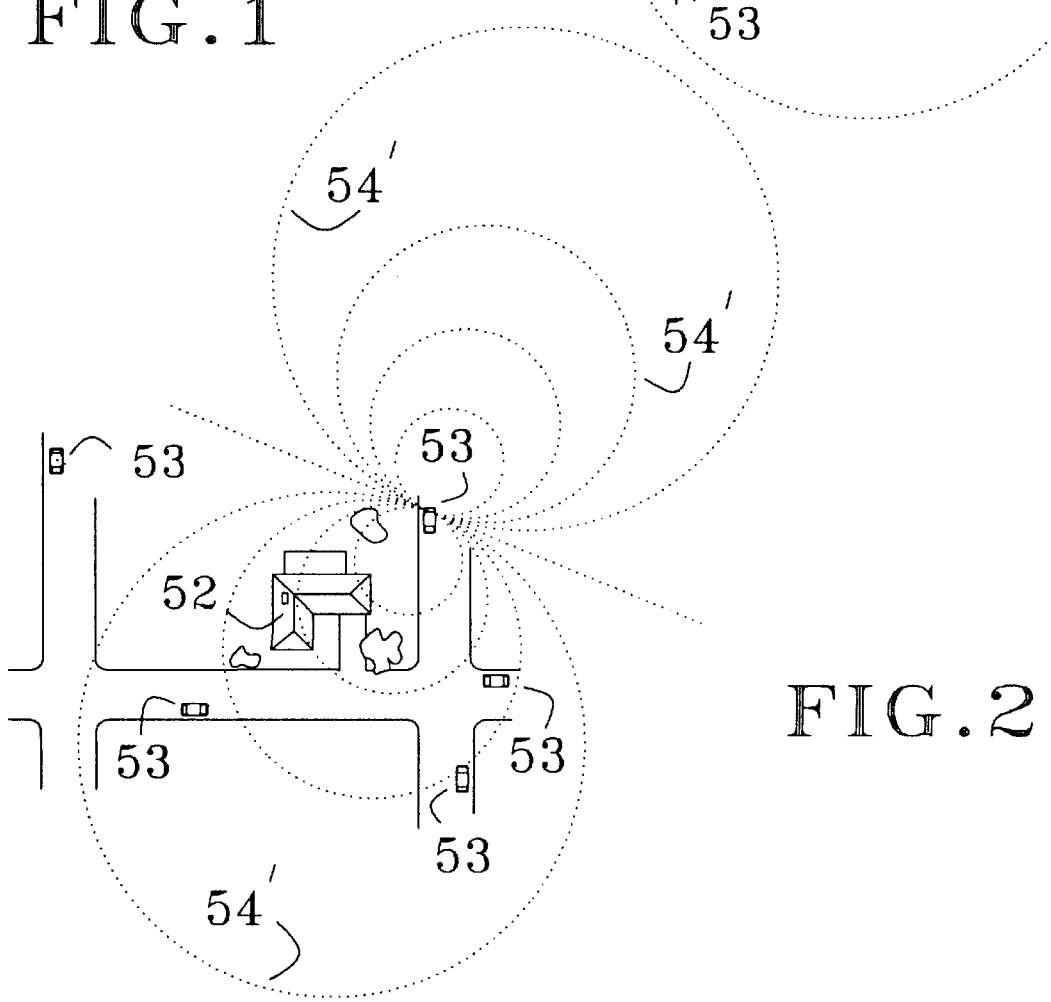
FIG. 2 shows how the dipole field of FIG. 1 has rotated in a a short time.

As aluded to earlier, rotating magnetic fields can also be used for remote systemic magnetic manipulation of the nervous system of a subject, "remote" meaning at a distance exceeding three meters. The dominant field far away from a magnet is a dipole field, which falls off as the third power of distance. The very small field strengths that suffice for magnetic excitation of sensory resonances, together with the large magnetic moments that can be achieved with permanent magnets, make remote magnetic manipulation of nervous systems with small and compact devices a practical possiblity. For instance, for a device of 20 cm overall diameter the magnetic moment of a fitting bar magnet can easily be as large as 52 $Am^2$, and such a magnet is capable of inducing a 0.39 pT magnetic field at a distance of 300 m. By tuning the magnet rotation to a sensory resonance frequency near ½ Hz, such a field amplitude is sufficient to cause drowsiness. The arrangement is thus suitable for a non-lethal weapon which may be used, for instance, in law enforcement standoff situations. Such an application is illustrated in FIG. 1, where subjects are holding out in a house 52. Shown are squad cars 53, one of which is equiped with a rotating magnet device. The magnetic dipole field emanating from the device is illustrated schematically by field lines 54. The rotation of the permanent magnet causes the magnetic field to rotate, and FIG. 2 shows field lines 54' a short time later, after the magnet has made a quarter turn. When the magnet rotation is tuned to the appropriate sensory resonance frequency, the oscillatory eddy currents induced in the subject's bodies may cause sleepiness, which would diminish the subject's alertness and clarity of thought. It is noted that the physiological effects of the magnetic excitation of sensory resonances appears to be larger when 60 or 50 Hz power fields are absent, so that there may be merit in turning off the electric power to the house, if this can be done safely and is not contraindicated by other considerations.

A suitable rotating magnet device may be designed along the following lines. The magnetic field projected upon the remote subject must have, at the large range involved, an amplitude in the effective intensity window. Since this field is predominantly of dipole nature, and is therefore approximately proportional to the magnetic moment of the magnet, it is advantageous to maximize the magnetic moment within the imposed constraints. The moment is the product of the distance between the magnetic poles and the strength of the poles, expressed as the emanating magnetic flux. Thus, other things remaining the same, the poles need to be as far away from each other as possible. Clearly, a horse-shoe magnet will not do; rather, the optimum configuration is a bar magnet. A second issue pertains to the orientation of the bar magnet with respect to the rotation axis. This orientation is expressed as the angle γ between the rotation axis and the bar magnet axis, defined as the line connecting the centers of the pole faces (this line is also the direction of the magnetic moment vector). Since the eddy currents induced in the body of the exposed subject are proportional to the rate of change of the magnetic field, the amplitude of the field oscillation needs to be maximized. This is done by choosing the angle γ as ninety degrees. The next question is how to choose the angle β between the rotation axis and the line that connects the magnet with the subject. To answer this question it must be noted that the field along the front direction of the magnet, i.e., along the magnet axis, is twice as large as the field along the side direction, i.e., ninety degrees away from the magnet axis. It follows that the angle β best be chosen as ninety degrees, because the field oscillation amplitude then benefits from the strong field along the front direction of the magnet.

A rotating magnet device designed along the aformentioned lines is illustrated in FIG. 3, which shows a shaft 62 that is free to spin in a bearing 63, and is driven by a stepper motor 78. The spinning motion may be continuous or may proceed in discrete steps. Mounted on the shaft is a bar magnet 55 with pole faces 57 and 58, that have polarities labelled "N" and "S". The bar magnet has an axis 79 that connects the centers of the pole faces. The angle γ between the magnet axis 79 and the axis 59 of the shaft 62 is substantially ninety degrees. A subject 4' is located remote, i.e., at least 3 meters, from the rotating magnet device. The device is oriented such that the angle β between the shaft axis 59 and the geometric straight line 56 that connects the shaft 62 with the subject 4' is substantially ninety degrees. To define the line 56 precisely, it is specified to go through points A and B, where point A is the position of the apparatus, taken as center of gravity of the shaft 62, and point B is the location of the subject, taken as the center of gravity of the body of the subject 4. The angles β and γ are not critical, and "substantially" may be read as "within 20 degrees". With the mentioned angle γ, the pole faces of the bar magnet will be substantially parallel to the shaft axis. Further shown are field lines 54 of the magnetic field induced by the bar magnet 55. As the latter is rotated by the stepper motor 78, the nearly uniform magnetic field induced in the body of the subject 4' varies in time, so that eddy currents are induced in the electrically conductive body.

One may use a composite bar magnet that consists of two magnets separated by a ferromagnetic spacer, for the purpose of inexpensively increasing the magnetic moment.

Driving circuitry for the rotating magnet of FIG. 3 is illustrated in FIG. 4, showing a clock 70 which generates a square wave train of clock pulses 71 that are processed by a counter 72 which outputs a pulse 50 at every Nth clock pulse, the integer N being provided by the output of a counter 73, and shown by the display 67. The integer N can be increased or decreased by push buttons 74 and 75, respectively labelled "UP" and "DOWN". The counter 73 together with the buttons 74 and 75 is therefore effectively a tuner for controlling the frequency of the pulses 50. These pulses are processed by the driver 77, connected to the stepper motor 78.

The law-enforcement personnel present at the standoff site will of course also be subjected to the rotating magnetic field, and this constitutes a major drawback of the method. The effective intensity window may relieve this problem to some extent, since the personnel experience large fields that may lie outside the window. Yet, frequent changes of personnel may be required in order to have an alert crew at all times.

Multiple devices may be used; all magnets then should rotate with the same frequency, although interesting beat effects arise when the individual frequencies are somewhat different. Use of multiple devices raises two new issues. Let all devices be located in the ground plane, i.e., a plane through the local ground surface, or, in hilly or mountanous terrain, tangent to the ground at the subject's location. Let devices n=1, 2, . . . m be located at $\theta_n$, $r_n$, where $(\theta,r)$ are polar coordinates in the ground plane, centered at the subject. The angle $\phi_n$ between the shaft axis of the nth device and the ground plane is pertinent and needs to be specified. For the setup depicted in FIGS. 1–3, the angle $\phi$ is ninety degrees. The second issue concerns phases. For the standard case with both $\beta$ and $\gamma$ equal to ninety degrees, the phase $\alpha_n$ of bar magnet n may be taken as the angle, at a fixed time, between the magnet axis and the line that connects the magnet with the subject; in FIG. 3 these lines are respectively shown as 79 and 56. It is advantageous to choose the phase angles $\alpha_n$ such that at the subject the magnetic fields induced by the individual rotating magnet devices interfere constructively, since that results in a larger total field oscillation amplitude. How to achieve this depends on the angles $\alpha_n$. One choice is to take all $\alpha_n$ zero, so that the magnets rotate in planes that are perpendicular to the ground plane. For m=2, the choice $\theta_1=0$, $\theta_2=\pi$ is advantageous, and should be used with a phase difference $\alpha_2-\alpha_1=\pi$. The fields at the subject then interfere constructively and result in a total oscillatory field amplitude that is the sum of the amplitudes for the single devices. For three devices located at about equally spaced angles $\theta_n$ around the circle one can take $\alpha_2-\alpha_1=\pi$ and $\alpha_3-\alpha_1=\pi$, and get considerable constructive interference, but for a larger number of devices placed at about equally spaced angles $\theta_n$ around the circle it is better to choose all $\phi_n$ equal to $\pi/2$ so that the magnets rotate in planes that are parallel to the ground plane and the field along the side directions of the magnets can contribute to constructive interference. Finding the optimum values for the phases $\alpha_n$ requires some work. To show how this may be done, consider a Cartesian coordinate system (x,y) in the ground plane, centered at the subject, such that the y-axis coincides with the direction $\theta=0$, with the the x-axis chosen such that rotation from the y-axis to the x-axis involves an increasing angle $\theta$. It can be easily shown that the magnetic field induced at the subject by the nth device has the Cartesian components $$B_{nx}=(\mu M_n/(4\pi r_n^3))\{\sin(\theta_n+\alpha_n+\omega t)-3\sin\theta\cos(\alpha_n+\omega t)\}, \quad (1)$$

$$B_{ny}=(\mu M_n/(4\pi r_n^3))\{\cos(\theta_n+\alpha_n+\alpha t)-3\cos\theta\cos(\alpha_n+\omega t)\}, \quad (2)$$

where $M_n$ is the magnetic moment of the nth magnet, the permeability $\mu$ should be taken as $4\pi\times10^{-7}$ henries/m, and t denotes time. The resultant magnetic field vector B is found by calculating the sum $B_x$ of the $B_{nx}$ for all n, and the sum $B_y$ of the $B_{ny}$ for all n; the vector B then has the components $B_x$ and $B_y$. As time proceeds, the end point of the vector B circulates with the radian frequency $\omega$ along an ellipse with long axis $2B_{max}$. The task at hand is to find the phase angles $\alpha_n$ that optimize $B_{max}$. This problem can be solved numerically with a grid of values $\alpha_n$; since the maximum in $B_{max}$ is rather broad, the grid can be chosen as coarse. Tables of solutions can be prepared once and for all for typical configurations involving a few rotating magnet devices. In practice, device configurations must be chosen such that $B_{max}$ lies in the effective intensity window for the chosen sensory resonance.

In the best mode no separate stepper motor is used, and the necessary torque on the magnet is supplied by magnetic fields induced by coils placed close to the magnet. This is illustrated in FIG. 5, where the bar magnet is composite, consisting of two permanent magnets 60 mounted on a ferromagnetic spacer 61, which is fastened to the shaft 62 that can rotate freely in bearings 63. Coils 64 are mounted such as to cause the magnet assembly to engage in a spinning motion, when pulsed currents are passed through the coils in properly phased manner. The currents are caused by a driver 65 connected to the coils by wires 66. The period of rotation of the magnet assembly is determined by the pulse frequency of the driver 76, and is shown by the display 67; the period can be changed by operating the up and down buttons 68 and 69. The driver may include a control unit 51 which can be programmed to provide a chosen schedule of activity times and frequencies. The driver and the control unit are standard circuits well known to those skilled in the art.

For military applications the device of FIG. 5, properly designed for compactness and for withstanding shock, can be air dropped or shot by mortar to locations near foes so that the latter can be subjected to magnetic manipulation. It is then suitable to arrange for radio control of the device. Since the rather slow rotation of a well-balanced magnet assembly can be maintained by small coil currents, battery power is viable. A startup circuit needs to be provided to get the magnet rotation going.

Human sensitivity to very weak magnetic fields at sensory resonance frequencies is not understood. U.S. Pat. No. 5,935,054 contains a discussion of several aspects of this problem. In addition, it is noted that cutaneous stretch receptors may be involved in the response to the weak magnetic fields, because the polarization charges that accumulate on surfaces of discontinuity of the electric conductivity as a result of the eddy currents decay slowest on the skin, if the subject is electrically isolated from the surroundings. Thermal smearing of the polarization charges in the epidermis over a layer with thickness of the order of the Debye length then may cause an electric field to act on susceptable stretch receptors that lie close to the epidermis or protrude from the dermis into the epidermis. This electric field oscillates with the frequency of the applied magnetic field and may perhaps cause frequency modulation of the spontaneous spiking of the stretch receptors.

The method is expected to be effective also on certain animals, and application to animal control is therefore envisioned. The nervous system of mammals is similar to that of humans, so that sensory resonances are expected to exist. The disposition towards the ½ Hz resonance is thought to have its origin in the fetal state, developed through the rythmical sensations caused by the mother's walk, associatively coupled with hormone concentrations. For mammals, one expects a resonance of this type at about the frequency of the mother's relaxed walk. Accordingly, in the present invention, the subjects are mammals.

The invention is not limited by the embodiments shown in the drawings and described in the specification, which are given by way of example and not of limitation, but only in accordance with the scope of the appended claims.

I claim:

1. Apparatus for manipulating the nervous system in the body of a remote subject, the subject having a location, and the apparatus having a position, a geometric straight line being defined through the position of the apparatus and the location of the subject, the apparatus comprising:

a shaft having an axis, the shaft being adapted to render substantially a ninety degree angle between the axis and the geometric straight line;

a bar magnet mounted on the shaft, the magnet having pole faces that are substantially parallel to the shaft axis, the bar magnet inducing in the body a nearly uniform magnetic field; and rotation means for spinning the shaft, whereby the nearly uniform magnetic field changes in time, and oscillatory eddy currents are induced in the body.

2. The apparatus of claim 1, further including control means for controlling the rotation means.

3. The apparatus of claim 2, wherein the spinning has an angular speed, and the control means comprise means for controlling the angular speed.

4. The apparatus of claim 1, wherein the bar magnet is composite.

5. The apparatus of claim 1, wherein the rotation means comprise coils for inducing a magnetic field that acts on the bar magnet.

6. A method for manipulating the nervous system in the body of a remote subject, the subject having a location, the method comprising the steps of:

mounting a bar magnet on a shaft, the shaft having a center of gravity and an axis, the axis having a direction, the bar magnet having pole faces that are substantially parallel with the shaft axis, the bar magnet inducing a nearly uniform magnetic field in the body;

defining a geometric straight line through the center of gravity and the location of the subject;

adapting the shaft for said direction to make an angle of substantially ninety degrees with the geometric straight line;

spinning the shaft;

whereby the nearly uniform magnetic field changes in time, and oscillatory eddy currents are induced in the body.

7. The method of claim 6 for exciting in the remote subject a sensory resonance having a resonance frequency, wherein the spinning has a frequency, further including the step of setting the spinning frequency to the resonance frequency.

8. The method of claim 6, wherein the steps of mounting, defining, adapting and spinning are repeated N times, N being a positive integer, resulting in bar magnets denoted by $M(i)$, i=1 to N+1, each with its geometric straight line $L(i)$, and wherein all spinning is done at the same rate, further including the steps of:

assigning, for each bar magnet $M(i)$, a magnet axis $A(i)$;

defining, for each bar magnet $M(i)$, a phase which at a fixed time is the angle of the magnet axis $A(i)$ with the geometric straight line $L(i)$; and arranging the phases of the bar magnets for constructive interference of the nearly uniform magnetic fields induced in the body.

\* \* \* \* \*